(12) United States Patent
Bar et al.

(10) Patent No.: US 10,258,491 B2
(45) Date of Patent: Apr. 16, 2019

(54) DEFORMABLE TIP FOR STENT DELIVERY AND METHODS OF USE

(71) Applicant: InspireMD, Ltd., Tel Aviv (IL)

(72) Inventors: Eli Bar, Moshav (IL); Dror Hazan, Petah Tikva (IL)

(73) Assignee: INSPIREMD, LTD., Tel Aviv (IL)

( * ) Notice: Subject to any disclaimer, the term of this patent is extended or adjusted under 35 U.S.C. 154(b) by 248 days.

(21) Appl. No.: 15/419,437

(22) Filed: Jan. 30, 2017

(65) Prior Publication Data

US 2017/0216066 A1    Aug. 3, 2017

Related U.S. Application Data

(60) Provisional application No. 62/290,031, filed on Feb. 2, 2016.

(51) Int. Cl.
*A61F 2/06* (2013.01)
*A61F 2/966* (2013.01)
*A61F 2/91* (2013.01)
*A61F 2/958* (2013.01)
*A61F 2/86* (2013.01)
*A61F 2/852* (2013.01)

(52) U.S. Cl.
CPC ............. *A61F 2/966* (2013.01); *A61F 2/91* (2013.01); *A61F 2/958* (2013.01); *A61F 2/852* (2013.01); *A61F 2/86* (2013.01); *A61F 2210/0004* (2013.01); *A61F 2210/0014* (2013.01); *A61F 2250/001* (2013.01); *A61F 2250/0067* (2013.01)

(58) Field of Classification Search
CPC .... A61F 2/06; A61F 2/86; A61F 2/966; A61F 2/91; A61F 2/958; A61F 2/95; A61F 2002/95; A61F 2002/9528
See application file for complete search history.

(56) References Cited

U.S. PATENT DOCUMENTS 3,692,029 A * 9/1972 Adair .................... A61M 25/04
                                                          604/105
4,512,762 A * 4/1985 Spears ................... A61B 17/22
                                                          604/21

(Continued)

OTHER PUBLICATIONS

WIPO, International Search Report and Written Opinion for International Application No. PCT/IB2017/050518, dated May 24, 2017.

*Primary Examiner* — Victor Nguyen
(74) *Attorney, Agent, or Firm* — Haynes and Boone, LLP (57) ABSTRACT

A stent-delivery assembly that includes a catheter; an expandable stent that is movable, relative to the catheter, from a first position to a second position; and a guidewire assembly extending through a longitudinal passage of the catheter and a longitudinal passage of the stent, the guidewire assembly being movable, relative to the catheter, from a third position to a fourth position. While the expandable stent is in the first position and while the guidewire assembly is in the third position, the stent-delivery assembly has an a-traumatic shape. While the expandable stent is in the second position and while the guidewire assembly is in the fourth position, the guidewire assembly is capable of passing through the stent to allow for retrieval of the stent-delivery assembly. Methods of use and manufacture are also included.

15 Claims, 4 Drawing Sheets

(56) References Cited

U.S. PATENT DOCUMENTS

| | | | |
|---|---|---|---|
| 4,706,671 A | * | 11/1987 | Weinrib ............... A61B 17/221 604/104 |
| 5,380,282 A | | 1/1995 | Burns |
| 2007/0276468 A1 | | 11/2007 | Holzer et al. |
| 2008/0140189 A1 | | 6/2008 | Nguyen et al. |
| 2008/0255652 A1 | | 10/2008 | Thomas et al. |
| 2009/0105801 A1 | | 4/2009 | Ivancev |

* cited by examiner

DEFORMABLE TIP FOR STENT DELIVERY AND METHODS OF USE

CROSS-REFERENCE TO RELATED APPLICATION(S)

This application claims the benefit of U.S. Provisional Patent Application No. 62/290,031, filed Feb. 2, 2016, now pending, the entire contents of which is hereby incorporated herein by express reference thereto.

FIELD OF THE DISCLOSURE

The present disclosure relates in general to a stent-delivery assembly and more specifically, to a stent-delivery assembly that has a deformable tip.

BACKGROUND

The placement of a stent within a vessel often includes pushing a stent-delivery assembly that houses the stent through narrow or tight portions of the vessel. If the stent-delivery assembly has a traumatic tip, or a tip that causes injury, damage, or irritation to the vessel, a portion of the vessel may be damaged during placement of the stent. The vessel may be damaged when the stent-delivery assembly enters the vessel or anytime during movement of the stent-delivery assembly within the vessel, including during removal. Generally, a balloon and a stent of the stent-delivery assembly will be placed in the vessel at a location coinciding with a lesion within the vessel. Thus, even if the stent-delivery assembly is small enough to avoid damaging the vessel, the stent-delivery assembly might dislodge or otherwise agitate the lesion when the stent passes through the lesion. Additionally, after placing the stent, the balloon must be pulled through the set stent before the stent-delivery assembly can be retrieved. Often, the balloon can "catch" on the stent while passing through the stent or otherwise be cut or damaged by the stent.

The present disclosure is directed to a stent-delivery assembly and methods that overcome one or more of the shortcomings in the prior art.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are methods and a stent-delivery assembly. In one or more exemplary embodiments, a stent-delivery assembly includes a catheter configured to deliver a stent at a distal end thereof and having a first longitudinal passage at the distal end and a catheter inner diameter; an expandable stent movable, relative to the catheter, from a first position to a second position, the expandable stent having a second longitudinal passage and a stent inner diameter; and a guidewire assembly extending through the first longitudinal passage and through the second longitudinal passage, the assembly movable, relative to the distal end of the catheter, from a third position to a fourth position, the guidewire assembly including: an inner lumen having an exterior surface; and a radially adjustable tip concentrically disposed about the exterior surface of inner lumen and including: a first end that is tapered towards the inner lumen and that is coupled to the inner lumen; an opposing second end; and a radially adjustable middle portion. In one embodiment, when the stent is in the first position, the stent is concentrically disposed within the first longitudinal passage and has a first stent inner diameter; when the stent is in the second position, the stent is spaced longitudinally from the first longitudinal passage of the catheter and has a second stent inner diameter that is greater than the first stent inner diameter; when the guidewire assembly is in the third position, the inner lumen is under tension, the opposing second end extends within the first longitudinal passage and the second longitudinal passage, and a portion of the radially adjustable middle portion of the tip has a first tip outer diameter that is greater than or equal to the catheter inner diameter; and when the guidewire assembly is in the fourth position, the opposing second end of the tip is spaced longitudinally from the first longitudinal passage of the catheter and the adjustable middle portion of the tip has a second tip outer diameter that is less than the first tip outer diameter and less than the second stent inner diameter. In another embodiment, when the guidewire assembly is in the third position, the expandable stent is in the first position; and when the expandable stent is in the second position, the guidewire assembly is in the fourth position. In yet another embodiment, the tip includes an elastic tip that is configured to accommodate a predetermined amount of a fluid. In one embodiment, when the guidewire assembly is in the third position, the stent compresses the tip so that the predetermined amount of fluid expands a portion of the radially adjustable middle portion such that the first tip outer diameter is greater than the catheter inner diameter; and when the guidewire assembly is in the fourth position, the tip is in a neutral state that is not radially constrained, permitting a predetermined amount of fluid to extend along a length of the tip and the second tip outer diameter to become less than the first tip outer diameter and less than the stent second inner diameter. In one embodiment, the predetermined amount of fluid includes at least one of a liquid and a gas. In yet another embodiment, the opposing second end of the tip is coupled to the inner lumen. In one embodiment, the opposing second end of the tip is tapered towards the inner lumen. In another preferred embodiment, compression of one portion of the radially adjustable middle portion results in another portion of the radially adjustable middle portion expanding to the first tip outer diameter. In yet another embodiment, the stent-delivery assembly is configured to be implanted in a vessel when the stent is in the first position and when the guidewire assembly is in the third position. In one embodiment, the opposing second end of the tip moves relative to the inner lumen. In another embodiment, the tip is a substantially cylindrical tip; and the radially adjustable middle portion has circumferentially-spaced, longitudinally-extending slots that define longitudinally extending leg portions. In yet another embodiment, the compression of the tip in the longitudinal direction results in the leg portions extending in a radial direction to the first tip outer diameter. In one embodiment, the tip has a first length when the guidewire assembly is in the third position and a second length that is greater than the first length when the guidewire assembly is in the fourth position. In another embodiment, each of the first end and the opposing second end forms an a-traumatic shape. In yet another embodiment, the tip is a substantially cylindrical tip or a cylindrical tip; and the radially adjustable middle portion comprises a braided material.

In a further aspect, the disclosure encompasses a guidewire assembly that includes an inner lumen having an exterior surface; a radially adjustable tip concentrically disposed about the exterior surface of the inner lumen and including a first end that is tapered towards the inner lumen and that is coupled to the inner lumen; an opposing second end; and a radially adjustable middle portion; and a cylindrical body concentrically disposed about and coupled to the exterior surface of the inner lumen, the body longitudinally spaced from the opposing second end of the tip along the inner lumen by a first distance. In one embodiment, the first distance is a function of a length of the stent. In another embodiment, the tip includes an elastic tip that is configured to accommodate a predetermined amount of a fluid. In yet another embodiment, the predetermined amount of fluid includes at least one of a liquid and a gas. In one embodiment, compression of one portion of the radially expandable middle portion results in the another portion of the radially expandable middle portion expanding. In one embodiment, the opposing second end of the tip is coupled to the inner lumen. In yet another embodiment, the opposing second end of the tip is tapered towards the inner lumen. In another embodiment, the opposing second end of the tip moves relative to the inner lumen. In yet another embodiment, the tip is cylindrical; and the radially adjustable middle portion has circumferentially-spaced longitudinally extending slots that define longitudinally extending leg portions. In one embodiment, compression of the tip in the longitudinal direction results in the leg portions extending radially. In yet another embodiment, the tip is a substantially cylindrical tip or a cylindrical tip; and the radially adjustable middle portion comprises a braided material.

In yet another aspect, the disclosure encompasses a method of manufacturing a stent-delivery assembly, the method including providing a catheter having a longitudinal passage and an inner diameter; concentrically disposing an expandable stent within the passage; extending a guidewire assembly through the passage, the guidewire assembly including: an inner lumen having an exterior surface; a radially adjustable tip concentrically disposed about the exterior surface of the inner lumen and including: a first end that is tapered towards the inner lumen and that is coupled to the inner lumen, the first end longitudinally spaced from the passage of the stent-delivery assembly; an opposing second end extending within the passage of the catheter; and an radially adjustable middle portion; pulling the tip towards the distal end of the catheter using the inner lumen; and compressing the tip using the stent such that the radially expandable middle portion expands to a diameter that is equal to or greater than the inner diameter of the catheter resulting in a stent-delivery assembly having an a-traumatic shape.

In another aspect, the disclosure encompasses a method of placing a stent, the method including: accommodating a stent-delivery assembly within a vessel, the stent-delivery assembly including: a catheter having a first longitudinal passage and having a stent-delivery assembly inner diameter; a guidewire assembly extending through the first longitudinal passage and movable, relative to the catheter, from a first position to a second position, the guidewire assembly including: an inner lumen having an exterior surface; a radially adjustable tip concentrically disposed about the exterior surface of the inner lumen and including: a first end that is tapered towards the inner lumen and that is coupled to the inner lumen; an opposing second end; and a radially adjustable middle portion; and an expandable stent concentrically disposed within the first longitudinal passage and having a second longitudinal passage, the inner lumen extending through the second longitudinal passage; moving the stent-delivery assembly relative to the vessel while the guidewire assembly is in the first position, wherein when the guidewire assembly is in the first position, the inner lumen is under tension, the opposing second end extends within the first longitudinal passage and the second longitudinal passage, and a portion of the radially adjustable middle portion of the tip has a first tip outer diameter that is greater than or equal to the stent-delivery assembly inner diameter; moving the guidewire assembly relative to the stent-delivery assembly in a first distal direction to the second position such that the stent is moved out of the first longitudinal passage and the stent expands such that the second longitudinal passage defines a stent inner diameter; wherein when the guidewire assembly is in the second position, the opposing second end of the tip is distally spaced longitudinally from the first longitudinal passage of the catheter and the radially adjustable middle portion of the tip has a second tip outer diameter that is less than the first tip outer diameter and less than the stent inner diameter; and moving the guidewire assembly relative to the catheter in a second direction that is opposite to the first direction such that the tip passes through the stent and towards the catheter. In one embodiment, the guidewire assembly is further selected to include a cylindrical body concentrically disposed about and coupled to the exterior surface of the inner lumen. In another embodiment, the tip is selected to be cylindrical; and wherein the radially adjustable middle portion is selected to have circumferentially-spaced longitudinally extending slots that define longitudinally extending leg portions. In yet another embodiment, the tip is selected to be cylindrical; and the radially adjustable middle portion is selected to comprise a braided material.

Various of these embodiments and those further discussed herein should be understood to be applicable to various aspects of the disclosure even if described only in connection with one particular aspect.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 1:
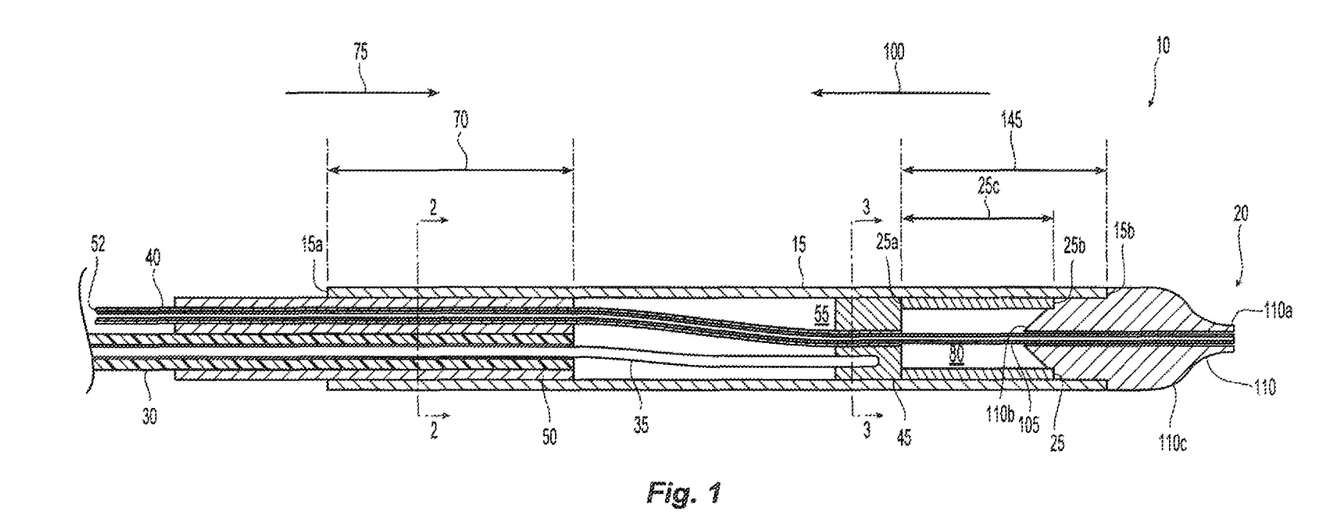
FIG. 1 is a sectional view of an apparatus according to one or more aspects of the present disclosure.
Figure 2:
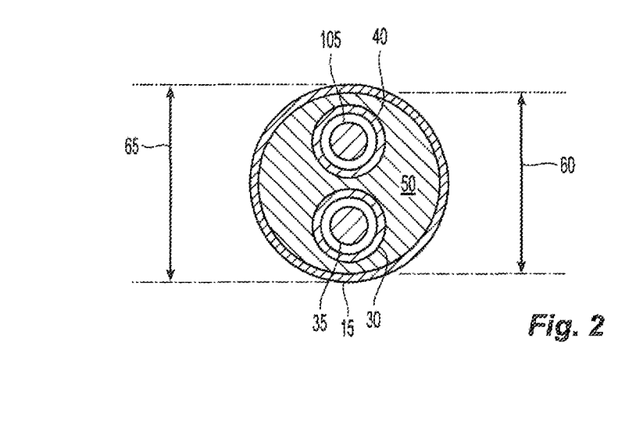
FIG. 2 is a cross sectional view of the apparatus of FIG. 1, according to one or more aspects of the present disclosure.
Figure 3:
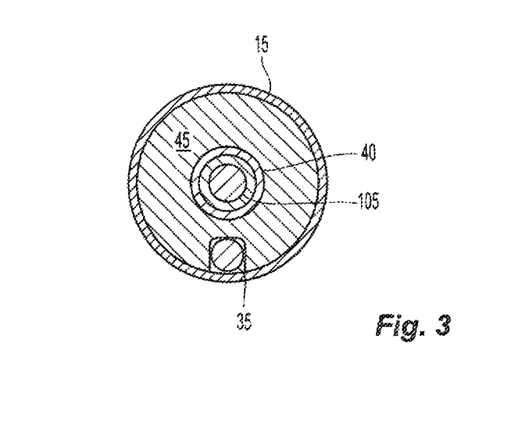
FIG. 3 is another cross sectional view of the apparatus of FIG. 1, according to one or more aspects of the present disclosure.

Referring to FIGS. 1-3, an apparatus 10 may generally include a catheter 15 through which a guidewire assembly 20 extends with a stent 25 disposed within the catheter 15. In an exemplary embodiment, the apparatus 10 also includes a hypo-tube 30, a push wire 35 extending within a portion of the hypo-tube 30, and an inner shaft 40 extending through at least a portion of the catheter 15 and coupled to a stent stop or a cylindrical body 45 that is concentrically disposed within the catheter 15. In an exemplary embodiment a lumen extrusion 50 is disposed within the catheter 15 and surrounds a portion of the inner shaft 40, the push wire 35, the hypo-tube 30, and a portion of the guidewire assembly 20. In an exemplary embodiment, the inner shaft 40 forms a rapid exchange (RX) port 52.

In an exemplary embodiment, the catheter 15 has a first end 15a and a second opposing end 15b. Additionally, the catheter 15 forms a longitudinal passage 55 defining a catheter inner diameter 60 shown in FIG. 2. In an exemplary embodiment, the catheter 15 has an outer diameter 65. In an exemplary embodiment, the catheter 25 includes a material manufactured by a process from the group consisting of interlacing knitting, interlocked knitting, braiding, interlacing, and/or dipping a porous mold into one or more reagents. In embodiments, the catheter 15 includes an elastomer such as a polyether block amide, such as Pebax®. In an exemplary embodiment, the catheter 15 includes a stainless steel braid with an elastomer surrounding the stainless steel braid.

In an exemplary embodiment, the lumen extrusion 50 includes a dual lumen extrusion that extends within and fills a portion of the longitudinal passage 55. In an exemplary embodiment, the dual lumen extrusion 50 is formed from a plastic material. However, the dual lumen extrusion may be formed from a variety of materials available to those of ordinary skill in the art and safe for use in a patient, e.g., a human patient. In an exemplary embodiment, the dual lumen extrusion 50 is coupled to the coupled to the catheter 15 such that the dual lumen extrusion 50 is stationary relative to the catheter 15. In an exemplary embodiment, the dual lumen extrusion 50 is bonded to the catheter 15. In an exemplary embodiment, the dual lumen extrusion 50 extends through the first end 15a of the catheter 15 and into the catheter 15 by a first distance 70 measured in a direction indicated by the numeral 75 illustrated in FIG. 1.

Figure 4:
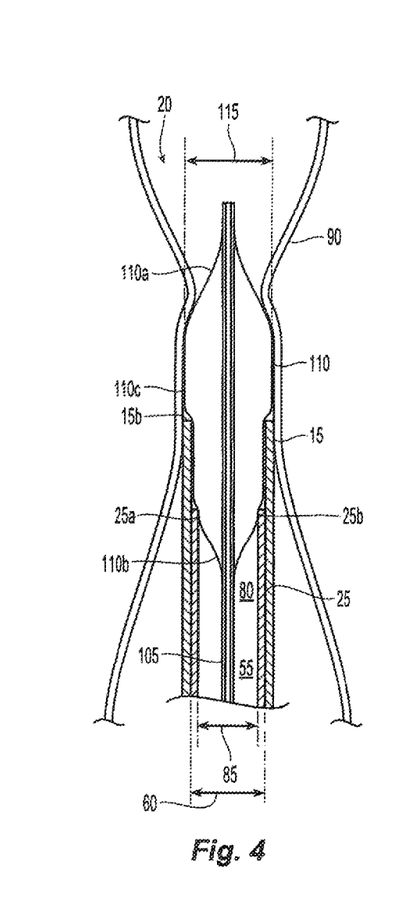
FIG. 4 is a sectional view of a portion of an apparatus when in a first position, according to an exemplary embodiment.
Figure 5:
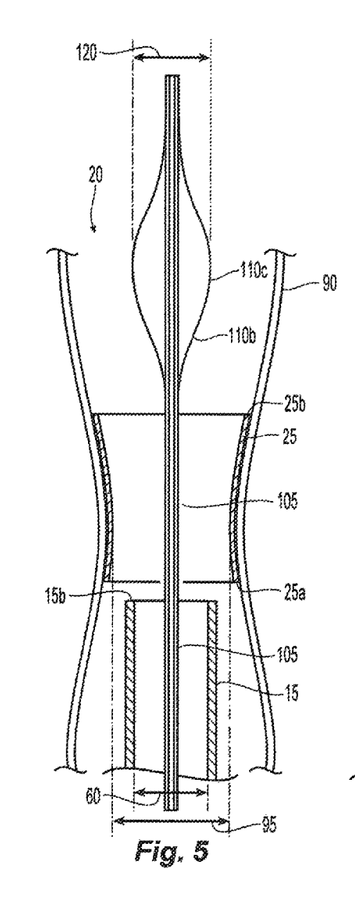
FIG. 5 is a sectional view of a portion of the apparatus of FIG. 4 when in a second position, according to an exemplary embodiment.

In an exemplary embodiment, the stent 25 is movable, relative to the second end 15b of the catheter 15, in the direction indicated by the numeral 75 illustrated in FIG. 1 to be disposed in the vessel and outside the catheter 15. In an exemplary embodiment, the stent 25 has a first end 25a and an opposing second end 25b that define a length 25c of the stent 25. In an exemplary embodiment, the stent 25 moves relative to the catheter 15 between a first position and a second position. These can be a first proximal position and a second distal position. In an exemplary embodiment and as illustrated in FIG. 4, when the stent 25 is in the first position, the stent 25 is disposed within the longitudinal passageway 55 of the catheter 15. In an exemplary embodiment, the stent 25 is an expandable stent having a second longitudinal passage 80 forming a stent inner diameter. In an exemplary embodiment, the second longitudinal passage 80 forms a portion of the first longitudinal passageway 55. In an exemplary embodiment, the stent 25 has a stent inner diameter 85 when in the first position. In an exemplary embodiment and as illustrated in FIG. 5, when the stent is in the second position, the stent 25 is no longer disposed within the longitudinal passageway 55 of the catheter 15. Instead, the stent 25 is spaced from the longitudinal passageway 55 and the second end 15b of the catheter 15. In the second distal position, the stent 25 is disposed within a vessel 90. As the stent 25 is no longer disposed within the longitudinal passageway 55, the stent 25 is free to expand within the vessel 90. In an exemplary embodiment, the stent 25 has a stent inner diameter 95 when in the second position. In an exemplary embodiment, the stent inner diameter 95 is larger than the stent inner diameter 85. Depending on the vessel 90, the stent 25 may expand to a diameter even larger than an outer diameter of the catheter.

In an exemplary embodiment, the stent 25 further includes a stent jacket (not shown) disposed concentrically over the stent 25. In a first position, the stent and stent jacket are inside the catheter 15. The stent jacket includes a mesh material, that in a preferred embodiment is manufactured interlacing knitting, interlocked knitting, braiding, interlacing, and/or dipping a porous mold into one or more reagents. An exemplary stent jacket (not shown) includes a mesh of polymer fibers having a diameter of about 10 microns to about 30 microns, with apertures of about 20 microns to 250 microns. In one embodiment, the apertures are about 20 up to 100 microns. In another embodiment, the apertures are at least 100 microns to about 225 microns. The polymer fiber preferably includes polyethylene terephthalate (PET), and preferably is formed substantially entirely or entirely of PET.

In an exemplary embodiment, the stent 25 may include any available medical stent, including a bare metal stent, drug eluting stent, coated stent (with or without an active pharmaceutical agent), etc. Therefore, and in some embodiments, the stent 25 is composed of a material that provides support, e.g., metal struts, or a sufficiently rigid polymer, which can be either a) stretchable and/or b) can be used to manufacture a porous structure which is stretchable. In some exemplary embodiments, the stent 25 is composed of a material that is biodegradable (i.e., are broken down by the body), bioresorbable (i.e., are absorbed into the body), or any combination thereof. In an exemplary embodiment, the stent 25 may be composed of a natural-based material, such as for example, modified cellulose and/or collagen. In some embodiments, the stent 25 may be composed of metal fibers used to construct a porous structure, optionally constructed of stainless steel, CoCr alloy, and/or CoNi alloy, among other possibilities. In an exemplary embodiment, the metal fibers (or the entire strand) used are coated with at least one polymer. In some embodiments, the porous structure is manufactured from a shape memory alloy, such as nitinol. In an exemplary embodiment, carbon fiber is added to the stent 25 in order to improve strength characteristics of stent 25. In an exemplary embodiment, glass fiber is added to the stent 25 in order to improve strength characteristics of the stent 25. In an exemplary embodiment, a durable, resorbable and/or degradable fiber is added to the stent 25 in order to improve strength and durability characteristics of the fiber during manufacture, which is degraded or resorbed or washed away to leave a thinner the stent 25.

In an exemplary embodiment, the catheter 15 and/or the stent 25 may be formed including polymer fibers. In an embodiment, the polymer fibers are chosen for use in constructing the catheter 15 and/or the stent 25 because they are elastic, biocompatible, hemocompatible, can be made not to stick to the tip 110 and/or the stent 25, to stick to endothelium tissue, are selectably bio-stable and/or biodegradable, exhibit the requisite mechanical strength, are sterilizable, have a high temperature transformation zone (solid and non sticky at 37° C.), and are capable of hosting an effective amount of one or more pharmaceutical agents, and/or can release embedded pharmaceuticals at a controlled rate, to prevent, minimize, treat, or manage a condition, disease, or symptom thereof, e.g., cardiac, arterial, coronary, etc. In some exemplary embodiments, other materials that exhibit some or all of these properties are optionally used to construct the catheter 15 and/or the stent 25. In an exemplary embodiment, coatings are put on the catheter 15 and/or the stent 25 that are formed including materials which exhibit some or all of these properties. In an exemplary embodiment, the polymer fibers are optionally made out of any of the following materials: thermoplastic polymers for example polyethylene terephthalate (PET), polyolefin, oxidized acrylic, PTFE, polyethylene co-vinyl acetate, polyethylene elastomer, PEO-PBT, PEO-PLA, PBMA, polyurethane, thermoplastic silicone polycarbonate urethane, (Carbosil®, a PTG product), medical grade polycarbonate urethanes, Nylon, PEEK-Optima®, carboxylic acid moiety including one or more of a poly-acrylic acid, a poly-methacrylic acid, a maleic acid, a helonic acid, a taconic acid and/or combinations and/or esters of these monomers, thermoplastic polymers, thermosetic polymers, polyolefin elastomers, polyesters, polyurethanes, polyfluoropolymers, and/or nylon, or any suitable combination of the foregoing. In an exemplary embodiment, the fibers are constructed of an elastomer. In an exemplary embodiment, the fibers are constructed of a coated fiber with a drug and polymer coating mixed to achieve a predetermined drug release characteristic, e.g., delayed release after a period of time, or a sustained release over a period of time, (from minutes to hours to weeks, to months), with the coating over a metal and/or over a polymer fiber. In an exemplary embodiment, the fibers are constructed of other materials than the exemplary materials listed above. Exemplary polymers which are optionally used for this purpose are manufactured by Cordis®, Surmodix®, Boston Scientific®, Abbott® and Hemoteq® polymers. In an exemplary embodiment, these polymers are selected for at least one of the reasons specified in the paragraph above. In an exemplary embodiment, the coating is used to facilitate the elution of pharmaceuticals from the catheter 15 and/or the stent 25 or from the stent jacket (not shown)). In some embodiments, the catheter 15 and/or the stent 25 or stent jacket is made out of a resorbable/degradable polymer such as poly lactic-co-polyglycolic ("PLGA") copolymers, or any other degradable copolymeric combination, such as polycaprolactone ("PCL"), polygluconate, polylactic acid-polyethylene oxide copolymers, poly (hydroxybutyrate), polyanhydride, poly-phosphoester, poly (amino acids), poly-L-lactide, poly-D-lactide, polyglycolide, poly(alpha-hydroxy acid) and combinations thereof.

In an exemplary embodiment, the guidewire assembly 20 is movable, relative to the second end 15b of the catheter 15, in the direction indicated by the numeral 75 illustrated in FIG. 1 and in an opposing direction indicated by the numeral 100 illustrated in FIG. 1. This can be a distal direction, used to implant the stent in a patient away from a proximal catheter insertion point. In an exemplary embodiment, the guidewire assembly 20 includes an inner lumen 105 having an exterior surface and a radially adjustable tip 110 concentrically disposed about the exterior surface of the inner lumen 105. In an exemplary embodiment, the tip 110 may include a first end 110a, an opposing second end 110b, and a radially adjustable middle portion 110c. In an exemplary embodiment, the first end 110a is coupled to the inner lumen 105 and tapered towards the inner lumen 105. In an exemplary embodiment, the middle portion 110c adjusts radially resulting in the outer diameter of the middle portion 110c changing, typically due to pressures applied on the tip 110, such as from the catheter 15, the stent 25, or a patient's vessel when the inner lumen 105 is in different positions. In an exemplary embodiment, the guidewire assembly 20 is movable relative to the catheter 15 between a first position and a second position. In an exemplary embodiment, when the guidewire assembly 20 is in the first position and as illustrated in FIG. 4, the stent 25 is in the first position, the inner lumen 105 is under tension, the opposing second end 110b extends within the longitudinal passages 55, 80, and a portion of the radially adjustable middle portion 110c of the tip 110 contacts the stent 25, and another portion of the radially adjustable middle portion 110c of the tip has a first outer diameter 115 that is greater than the catheter inner diameter 60. Thus, the tip 110 creates an a-traumatic shape for the apparatus 10 that both retains the stent 25 in the catheter 15 until a delivery location, and tapers toward a distal end of the inner lumen 105. In an exemplary embodiment, when the guidewire assembly 20 is in the second position as illustrated in FIG. 5, the opposing second end 110b of the tip 110 is spaced longitudinally from the longitudinal passage 55 of the catheter 15 and the second end 15b of the catheter 15 (typically in a distal direction from the entry point of the catheter into the vessel), and the adjustable middle portion 110c of the tip 110 has a second outer diameter 120 that is less than the catheter inner diameter 60 and less than the stent inner diameter 95 when the stent 25 is in the second position. In an exemplary embodiment, the second outer diameter 120 is associated with the tip 110 being in a neutral or natural state. In an exemplary embodiment, the tip 110 is in the neutral state when compression and/or tension forces acting upon the tip 110 are equal or substantially equal (i.e., within 10%) along the length of the tip 110. In an exemplary embodiment, the second outer diameter 120 of the tip 110 is less than the catheter inner diameter 60 and less than the stent inner diameter 95 when the tip 110 is in the neutral state. In an exemplary embodiment and when the tip 110 is in the second position (as illustrated in FIG. 5), the stent 25 is in the second position.

In an exemplary embodiment and as illustrated in FIGS. 4 and 5, the tip 110 is an "elastic" or deformable, tip. In an exemplary embodiment, the elastic tip 110 is formed including an "elastic" material, which can include natural and synthetic polymers (e.g., thermoset and thermoplastic elastomers including without limitation rubbers such as (poly)isoprene, (poly)chloroprene, butyl rubber, styrene-butadiene, nitrile copolymers of butadiene and acrylonitrile, silicone and fluorosilicone, (poly)acrylic, epichlorohydrin, ethylene propylene and ethylene-propylene-diene, and polysulfide rubber; and ethylene-vinyl acetate, (poly)ethylene, (poly)ether block amides (PEBA), perfluoroelastomers, fluoroelastomers, (poly)propylene units, and any combination of the foregoing, that can return towards their original shape spontaneously after deformation. It should be understood that various materials noted above may be crosslinked or uncrosslinked, as needed to achieve desired characteristics such as elasticity, as well as halogenated, such as halogenated butylene rubbers, e.g., chloro-butyl rubber and bromo-butyl rubber, chlorosulfonated polyethylene, and the like.

In an exemplary embodiment, the first end 110a and the second end 110b of the elastic tip 110 are coupled to the inner lumen 105. In an exemplary embodiment, the elastic tip 110 is configured or adapted to accommodate a predetermined amount of a fluid. In an exemplary embodiment, the fluid includes at least one of a liquid and a gas. In an exemplary embodiment, the second end 110b is tapered towards the inner lumen 105. In an exemplary embodiment, each of the first end 110a and the second end 110b form an a-traumatic shape. In an exemplary embodiment and when in the first position, the inner lumen 105 pulls the elastic tip 110 towards the first end 15a of the catheter 15. As the second end 110b is coupled to the inner lumen 105, the second end 110b is pulled into the longitudinal passage 55 of the catheter 15 and into the longitudinal passage 80 of the stent 25. In an exemplary embodiment and considering that each of the first end 110a and the second end 110b is coupled to the inner lumen 105, the length of the elastic tip 110 while the tip 110 is in the first position is the same as when the tip 110 is in the second position. Considering the first outer diameter 115 of the elastic tip 110 is greater than the stent inner diameter 85 of the stent 25 when the stent 25 in the first position, an interior surface of the stent 25 and/or the second end 25b of the stent 25 compresses at least a portion of the middle portion 110c as the elastic tip 110 is pulled towards the first end 15a of the catheter 15. In an exemplary embodiment, radial compression to at least a portion of the middle portion 110c results in the fluid within the tip 110 expanding another portion of the middle portion 110c to the first outer diameter 115. Thus, the elastic tip 110 is no longer in the neutral state. In an exemplary embodiment, the first outer diameter 115 of the tip 110 is equal to or greater than the catheter inner diameter 60. In an exemplary embodiment and as shown in FIG. 5, when the elastic tip 110 is in the second position, the second end 110b of the elastic tip 110 is spaced longitudinally from the second end 15b of the catheter 15 and the longitudinal passage 55 of the catheter 15. Additionally, the stent 25 is in the second position and has the stent inner diameter 95, which is larger than the second outer diameter 120 of the elastic tip 110. Thus, the stent 25 is no longer compressing the elastic tip 110 and the elastic tip 110 reverts to the neutral state. In an exemplary embodiment, the elastic tip 110 may be a torus bonded around the inner lumen 105. In an exemplary embodiment, the volume of the fluid within the tip allows for the tip 110 to change shape between the first position and the second position. In an exemplary embodiment, the tapered shape of the second end 110b encourages safe passage through the deployed stent 25 (i.e., when the stent 25 is in the second position) and into the catheter 15. Additionally, movement of the inner lumen 105 moves the elastic tip 110 before the fluid within the tip 110 moves. Therefore, the fluid within the elastic tip 110 can accumulate near the first end 110a such that the tip 110 forms a tear-drop shape (with the apex pointing in the direction 100) if the inner lumen 105 is pulled in the direction 100 and the fluid within the elastic tip 110 can accumulate near the second end 110b to form a tear-drop shape (with the apex pointing in the direction 75) if the inner lumen 105 is pushed in the direction 75. This encourages a leading end of the tip 110 to form an a-traumatic shape.

Figure 6:
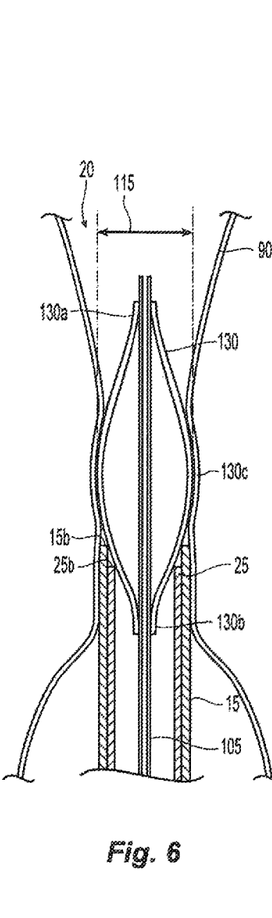
FIG. 6 is a sectional view of a portion of another apparatus including a tip when in a first position, according to an exemplary embodiment.
Figure 7:
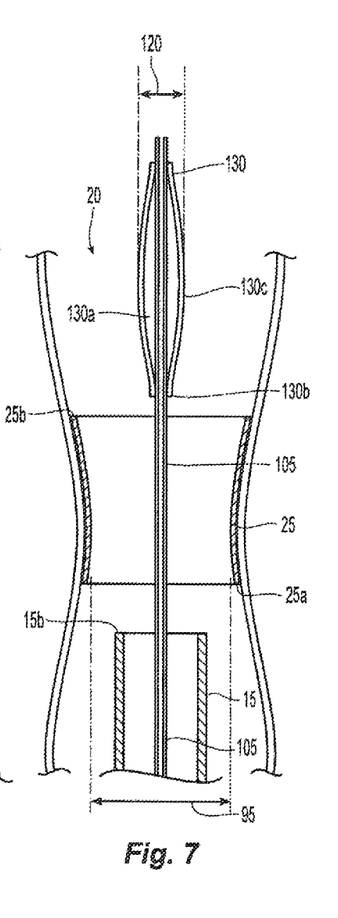
FIG. 7 is a sectional view of the portion of the another apparatus of FIG. 6 when in a second position, according to an exemplary embodiment.
Figure 8:
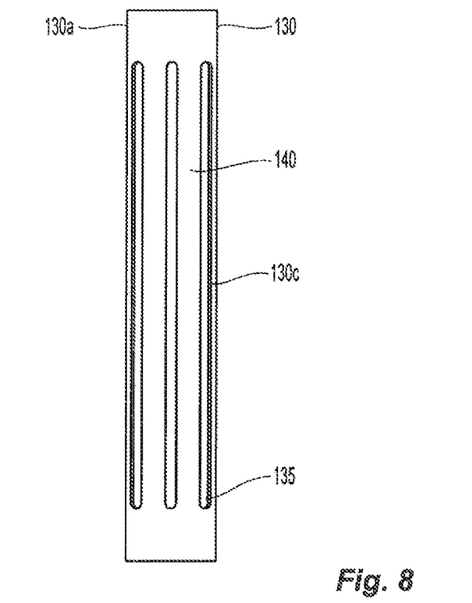
FIG. 8 is a side view of the tip of FIG. 6, according to an exemplary embodiment.

In another exemplary embodiment and as illustrated in FIGS. 6-8, the tip 110 may be a "Chinese lantern" type tip 130 that has a first end 130a, an opposing second end 130b, and a radially adjustable middle portion 130c. In an exemplary embodiment, the opposing second end 130b of the tip 130 may be movable relative to the inner lumen 105. In an exemplary embodiment, the tip 130 may be a substantially cylindrical tip and the middle portion 130c may have circumferentially-spaced, longitudinally extending slots 135 that define longitudinally extending leg portions 140. In an exemplary embodiment, compression of the tip 130 in the longitudinal direction results in the leg portions 140 extending in the radial direction to the first outer diameter 115. That is, in the first state, the inner lumen 105 pulls the first end 130a of the tip 130 towards the first end 15a of the catheter 15. As the stent inner diameter 85 of the stent 25 when the stent 25 in the first position is less than the second outer diameter 120 of the tip 130 when the tip 130 is in the neutral state, the tip 130 becomes lodged in the stent 25 and/or distal end of the catheter 15. Pulling on the inner lumen 105 results in longitudinal compression of the tip 130, which result in the leg portions 140 extending radially such that the tip 130 has the first outer diameter 115. In an exemplary embodiment, the tip 130 has a length in the second position that is greater than the length of the tip 130 while in the first position. In an exemplary embodiment, the tip 130 may be composed of any suitable deformable metal or plastic (including alloys, blends, or any other combination of material) available to those in the art, and may be manufactured using molding, cutting, injection, etc.

Figure 9:
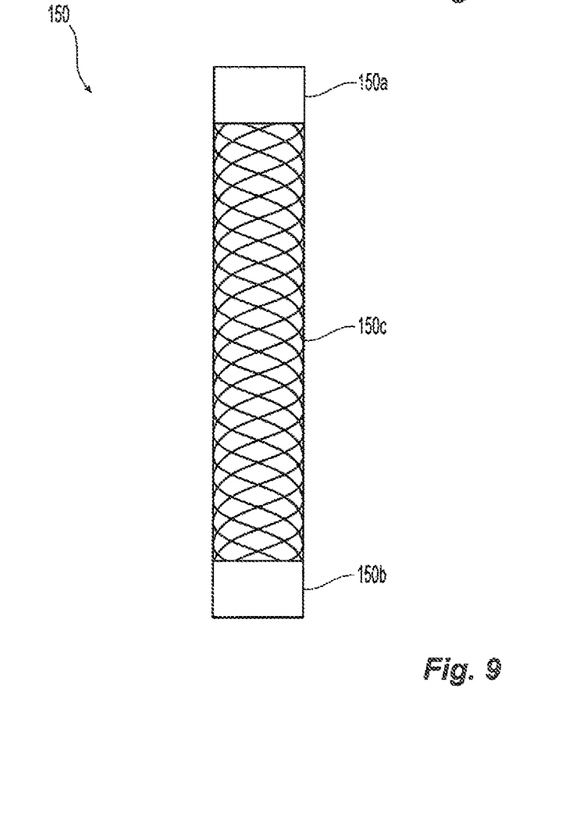
FIG. 9 is a side view of the apparatus of FIG. 6, according to another exemplary embodiment.

In another exemplary embodiment and as illustrated in FIG. 9, the tip 110 may be a "braided mesh" type tip 150 that has a first end 150a, an opposing second end 150b, and a radially adjustable middle portion 150c. In an exemplary embodiment, the opposing second end 150b of the tip 150 may be movable relative to the inner lumen 105. In an exemplary embodiment, the tip 150 may be a substantially cylindrical tip and the middle portion 150c may include a braided mesh material or collapsible, mesh-like material. In an exemplary embodiment, compression of the tip 150 in the longitudinal direction results in the middle portion 150c extending in the radial direction to the first outer diameter 115. That is, in the first state, the inner lumen 105 pulls the first end 150a of the tip 150 towards the first end 15a of the catheter 15. As the stent inner diameter 85 of the stent 25 when the stent 25 in the first position is less than the second outer diameter 120 of the tip 150 when the tip 150 is in the neutral state, the tip 150 becomes lodged in the stent 25 and/or distal end of the catheter 15. Pulling on the inner lumen 105 results in longitudinal compression of the tip 150, which result in the middle portion 150c extending radially such that the tip 150 has the first outer diameter 115. In an exemplary embodiment, the tip 150 has a length in the second position that is greater than the length of the tip 150 while in the first position. In an exemplary embodiment, the tip 150 may be composed of any suitable deformable metal or plastic (including alloys, blends, or any other combination of material) available to those in the art, and may be manufactured using molding, cutting, injection, etc.

In an exemplary embodiment, the inner shaft 40 forms a longitudinal passage sized to accommodate the inner lumen 105. In an exemplary embodiment, the inner shaft 40 is formed from a plastic material.

In an exemplary embodiment, the hypo-tube 30 extends through the first end 15a of the catheter 15 and through the dual lumen extrusion 50. In an exemplary embodiment, the hypo-tube 30 is coupled to the dual lumen extrusion 50. In an exemplary embodiment, the hypo-tube 30 is bonded to the dual lumen extrusion 50. In an exemplary embodiment, the hypo-tube 30 forms a longitudinal passage sized to accommodate the push wire 35.

In an exemplary embodiment, the push wire 35 extends through the longitudinal passage of the hypo-tube 30, with one end of the push wire 35 coupled to the cylindrical body 45. In an exemplary embodiment, the push wire is formed including a sufficiently stiff metal, such as stainless steel, to guide the catheter into a patient's lumen to a desired treatment location.

In an exemplary embodiment, the cylindrical body 45 extends within a portion of the longitudinal passage 55 of the catheter 15 and is movable in the direction 75 and 100 illustrated in FIG. 1 relative to the catheter 15. In an exemplary embodiment, the cylindrical body 45 includes a metal, such as stainless steel. However, a variety of other metals or other suitable safe materials are contemplated for use in various embodiments. In an exemplary embodiment, the cylindrical body 45 is disposed about and coupled to an exterior surface of the inner lumen 105 and to the push wire 35. In an exemplary embodiment, the cylindrical body 45 is spaced from the second end 15b of the catheter 15 by a distance 145 that is a function of a length 25c of the stent 25.

In an exemplary embodiment, the inner lumen 105 and/or the inner shaft 40 form a portion of a rapid exchange or RX port such that the apparatus 10 is a rapid exchange-type stent-delivery assembly.

Figure 10:
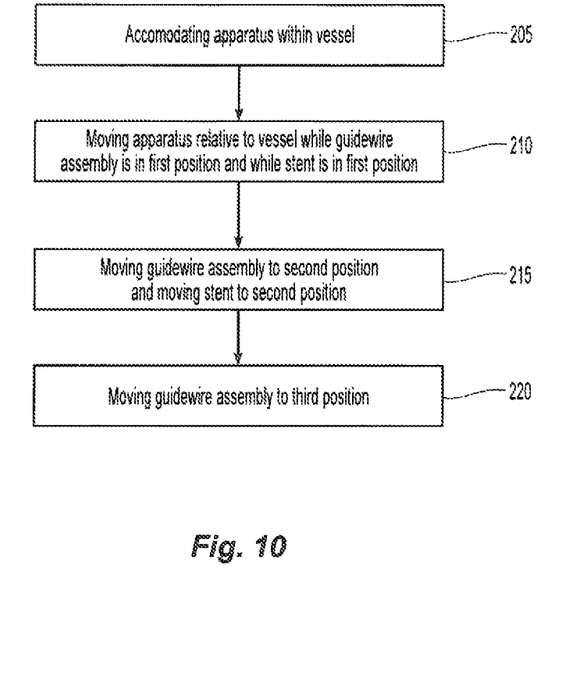
FIG. 10 is a flow chart illustration that describes a method of operating the apparatus of FIG. 1, according to an exemplary embodiment.

In an exemplary embodiment, as illustrated in FIG. 10 with continuing reference to FIGS. 1-5, a method of operating the apparatus 10 is generally referred to by reference numeral 200. In an exemplary embodiment, the method 200 includes accommodating the apparatus 10 within the vessel 90 at step 205; moving the apparatus 10 relative to the vessel 90 while the guidewire assembly 20 is in a first position and while the stent 25 is in the first position at step 210; moving the guidewire assembly 20 to a second position and moving the stent 25 to the second position at step 215; moving the guidewire assembly 20 to a third position at step 220.

At the step 205, the apparatus 10 is accommodated within the vessel 90. In an exemplary embodiment, the guidewire assembly 20 is in the first position and the stent 25 is in the first position while the apparatus 10 is accommodated within the vessel 90.

At the step 210 and as illustrated in FIG. 4, the apparatus 10 is moved relative to the vessel 90 while the guidewire assembly 20 is in a first position and while the stent 25 is in the first position. In an exemplary embodiment, the vessel 90 or a portion thereof may have an inner diameter that is smaller than an outer diameter of the apparatus 10. Thus, an a-traumatic shape of the apparatus 10 is beneficial when moving the apparatus 10 relative to the vessel 90. In an exemplary embodiment, the tip 110 while in the first position creates a tapered and smooth shape to a distal end of the apparatus 10, thus creating less irritation and possible damage to the vessel 90.

At the step 215 and as illustrated in FIG. 5, the guidewire assembly 20 is moved from the first position to the second position and the stent 25 is moved from the first position to the second position. In an exemplary embodiment, the push wire 35 is moved in the direction 75 which moves the cylindrical body 45 in the direction 75 relative to the catheter 15. Thus, the stent 25 is pushed from the first position to the second position and the guidewire assembly 20 is moved from the first position to the second position. As the stent 25 is no longer constricted by the catheter 15 while in the second position, the outer diameter of the stent 25 expands to the second diameter 95. In an exemplary embodiment, the stent 25 being in the second position is associated with the final placement or deployment of the stent 25 in the vessel 90, for example, where the stent 25 expands to an inner diameter of the vessel 90. In an exemplary embodiment, the second diameter 95 of the stent 25 is greater than the second outer diameter 120 of the tip 110 while in the neutral state.

At the step 220, the guidewire assembly 20 is moved to a third position. After the stent 25 has been deployed within the vessel 90, or once it is in the second position, the tip 110 is retracted in the opposite direction and the apparatus 10 is removed from the vessel 90. While in the second position, the inner diameter 95 of the stent 25 may be a rough surface or have struts or other features. As the second outer diameter 120 of the tip 110 while in the neutral state is less than the inner diameter 95 of the stent 25 while in the second state, the tip 110 is capable of passing through the deployed stent 25 while avoiding contact with the inner surface of the stent 25. Thus, the tip 110 may pass through the deployed stent 25 by pulling the inner lumen 105 in the direction 100. This can advantageously minimize or avoid the risk of dislodging the stent 25 once it is deployed in the vessel 90.

In an exemplary embodiment, the method 200 allows for placement of a stent 25 using a tapered and a-traumatic shaped apparatus 10. In an exemplary embodiment, the method 200 allows for a safe passage or retrieval of the tip 110 through the expanded or deployed stent 25. In an exemplary embodiment, the method 200 and/or the apparatus 10 allows for the tip 110 to retract through the deployed stent 25 while avoiding the interior diameter of the stent 25. In an exemplary embodiment, the method 200 allows the apparatus 10, or the stent-delivery assembly, to be pushed through narrow or tight vessels. In an exemplary embodiment, the vessel 90 may have an inner diameter that is smaller than the outer diameter 65 of the catheter 15 and the a-traumatic shape of the apparatus 10 allows for the apparatus 10 to pass through the vessel 90. In an exemplary embodiment, the stent 25 may have an inner surface that is not smooth once the stent 25 is deployed. Thus, the tip 110 having a second outer diameter 120 that is less than the inner diameter 95 of the stent 25 allows for the tip 110 to pass through the expanded stent 25 to aid in removal of the catheter 15.

In several exemplary embodiments, the elements and teachings of the various illustrative exemplary embodiments may be combined in whole or in part in some or all of the illustrative exemplary embodiments. In addition, one or more of the elements and teachings of the various illustrative exemplary embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several exemplary embodiments, while different steps, processes, and procedures are described as appearing as distinct acts, one or more of the steps, one or more of the processes, and/or one or more of the procedures may also be performed in different orders, simultaneously and/or sequentially. In several exemplary embodiments, the steps, processes and/or procedures may be merged into one or more steps, processes and/or procedures.

In several exemplary embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several exemplary embodiments have been described in detail above, the embodiments described are exemplary only and are not limiting, and those skilled in the art will readily appreciate that many other modifications, changes and/or substitutions are possible in the exemplary embodiments without materially departing from the novel teachings and advantages of the present disclosure. Accordingly, all such modifications, changes and/or substitutions are intended to be included within the scope of this disclosure as defined in the following claims. In the claims, any means-plus-function clauses are intended to cover the structures described herein as performing the recited function and not only structural equivalents, but also equivalent structures.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to allow the reader to quickly ascertain the nature of the technical disclosure. It is submitted with the understanding that it will not be used to interpret or limit the scope or meaning of the claims.

What is claimed is:

1. A stent-delivery assembly comprising:
   a catheter configured to deliver a stent at a distal end thereof and having a first longitudinal passage at the distal end and a catheter inner diameter;
   an expandable stent movable, relative to the catheter, from a first position to a second position, the expandable stent having a second longitudinal passage and a stent inner diameter; and
   a guidewire assembly extending through the first longitudinal passage and through the second longitudinal passage, the assembly movable, relative to the distal end of the catheter, from a third position to a fourth position, the guidewire assembly comprising:
   an inner lumen having an exterior surface; and
   a radially adjustable tip concentrically disposed about the exterior surface of the inner lumen and comprising:
   a first end that is tapered towards the inner lumen and that is coupled to the inner lumen;
   an opposing second end; and
   a radially adjustable middle portion;
   wherein when the stent is in the first position, the stent is concentrically disposed within the first longitudinal passage and has a first stent inner diameter;
   wherein when the stent is in the second position, the stent is spaced longitudinally from the first longitudinal passage of the catheter and has a second stent inner diameter that is greater than the first stent inner diameter;
   wherein when the guidewire assembly is in the third position, the inner lumen is under tension, the opposing second end extends within the first longitudinal passage and the second longitudinal passage, and a portion of the radially adjustable middle portion of the tip has a first tip outer diameter that is greater than or equal to the catheter inner diameter; and
   wherein when the guidewire assembly is in the fourth position, the opposing second end of the tip is spaced longitudinally from the first longitudinal passage of the catheter and the adjustable middle portion of the tip has a second tip outer diameter that is less than the first tip outer diameter and less than the second stent inner diameter.

2. The stent-delivery assembly of claim 1,
   wherein when the guidewire assembly is in the third position, the expandable stent is in the first position; and
   wherein when the guidewire assembly is in the fourth position, the expandable stent is in the second position.

3. The stent-delivery assembly of claim 1, wherein the tip comprises an elastic tip that is configured to accommodate a predetermined amount of a fluid.

4. The stent-delivery assembly of claim 3,
   wherein when the guidewire assembly is in the third position, the stent compresses the tip so that the predetermined amount of fluid expands a portion of the radially adjustable middle portion such that the first tip outer diameter is greater than the catheter inner diameter; and
   wherein when the guidewire assembly is in the fourth position, the tip is in a neutral state that is not radially constrained, permitting a predetermined amount of fluid to extend along a length of the tip and the second tip outer diameter to become less than the first tip outer diameter and less than the stent second inner diameter.

5. The stent-delivery assembly of claim 3, wherein the predetermined amount of fluid comprises at least one of a liquid and a gas.

6. The stent-delivery assembly of claim 3, wherein the opposing second end of the tip is coupled to the inner lumen.

7. The stent-delivery assembly of claim 6, wherein the opposing second end of the tip is tapered towards the inner lumen.

8. The stent-delivery assembly of claim 3, wherein compression of one portion of the radially adjustable middle portion results in another portion of the radially adjustable middle portion expanding to the first tip outer diameter.

9. The stent-delivery assembly of claim 1, wherein the stent-delivery assembly is configured to be inserted in a vessel when the stent is in the first position and when the guidewire assembly is in the third position.

10. The stent-delivery assembly of claim 1, wherein the opposing second end of the tip moves relative to the inner lumen.

11. The stent-delivery assembly of claim 10,
wherein the tip is a substantially cylindrical tip; and
wherein the radially adjustable middle portion has circumferentially-spaced, longitudinally-extending slots that define longitudinally extending leg portions.

12. The stent-delivery assembly of claim 11, wherein the compression of the tip in the longitudinal direction results in the leg portions extending in a radial direction to the first tip outer diameter.

13. The stent-delivery assembly of claim 10, wherein the tip has a first length when the guidewire assembly is in the third position and a second length that is greater than the first length when the guidewire assembly is in the fourth position.

14. The stent-delivery assembly of claim 10,
wherein the tip is a substantially cylindrical tip; and
wherein the radially adjustable middle portion comprises a braided material.

15. The stent-delivery assembly of claim 1, wherein each of the first end and the opposing second end forms an a-traumatic shape.

* * * * *